United States Patent [19]
Findlay

[11] Patent Number: 5,174,726
[45] Date of Patent: Dec. 29, 1992

[54] LIQUID PUMP

[76] Inventor: Iain S. Findlay, c/o Midcontinent Laboratories, Inc. 1010 Common St., Suite 3100, New Orleans, La. 70112

[21] Appl. No.: 659,859

[22] Filed: Feb. 22, 1991

Related U.S. Application Data

[63] Continuation-in-part of Ser. No. 402,676, Sep. 5, 1989, abandoned.

[51] Int. Cl.$^5$ .................................................. F04C 13/14
[52] U.S. Cl. ..................................... 417/205; 415/90; 415/900; 417/423.4; 417/423.7
[58] Field of Search .................. 415/90, 900; 417/203, 417/205, 420, 423.4, 423.5, 423.7

[56] References Cited

U.S. PATENT DOCUMENTS

| | | | |
|---|---|---|---|
| 1,058,790 | 4/1913 | Pierce | 415/90 |
| 1,061,142 | 5/1913 | Tesla | 415/90 |
| 2,998,099 | 8/1961 | Hollingsworth | 415/90 |
| 3,007,311 | 11/1961 | Amero | 415/90 X |
| 3,864,055 | 2/1975 | Kletschka et al. | 415/90 X |
| 3,957,389 | 5/1976 | Rafferty et al. | 415/900 X |
| 4,347,032 | 8/1982 | Possell | 415/90 |
| 4,688,998 | 8/1987 | Olsen et al. | 415/900 X |

Primary Examiner—Leonard E. Smith
Attorney, Agent, or Firm—Wood, Phillips, VanSanten, Hoffman & Ertel

[57] ABSTRACT

A two stage centrifugal and shear pump is characterized by low turbulence for pumping delicate liquids, as blood. Centrifugal first stage is a hollow shaft on which the shear pump discs are mounted. Offset slots in the shaft and disc hubs direct liquid out of the shaft to the discs.

32 Claims, 4 Drawing Sheets

LIQUID PUMP

CROSS REFERENCE

This is a continuation-in-part of U.S. patent application Ser. No. 402,676, filed Sep. 5, 1989, now abandoned.

FIELD OF THE INVENTION

This invention relates to a pump with minimal turbulence for delicate or volatile liquid. Blood, for example, is a delicate liquid having constituents which may be damaged by turbulence or mechanical pumping forces. The embodiments of the pump illustrated and described in the application combine high capacity with small size. The pump may be used in an implanted cardiac assist system.

BACKGROUND OF THE INVENTION

One class of rotary blood pump, particularly intended for extracorporeal use, has a shear pump impeller with curved, conical rotating elements. Struts extend radially or axially between the elements to provide structural support. Such pumps are shown in Kletschka U.S. Pat. No. 3,864,055, Rafferty U.S. Pat. No. 3,647,324 and Belanger U.S. Pat. No. 4,507,048. Blood pumps incorporating a conical shear impeller are sold under the Bio-Pump trademark by Bio-Medicus, Minneapolis, Minn. Another form of multi element shear or disc pump is shown in Effenberger U.S. Pat. No. 4,402,647.

The single stage pumps of the prior art have limited capacity. When operated at high rotary speeds, the intraelement struts cause turbulence.

SUMMARY OF THE INVENTION

The pump disclosed and claimed herein differs from the prior art pumps primarily in the combination of a centrifugal first stage with an inlet to receive liquid and an outlet to discharge liquid and a shear pump second stage having an inlet joined with a centrifugal outlet to receive liquid therefrom and an outlet to deliver liquid to the housing outlet. More particularly, the centrifugal pump has a hollow rotatable shaft connected with the first stage inlet and having an outlet slot (or slots) therein through which liquid is directed to the shear pump second stage. The shear pump is a plurality of parallel discs on the rotor, spaced apart at their centers to provide an inlet at which liquid is received from the centrifugal pump, the discs being spaced apart at their peripheries to provide an outlet from which liquid is delivered to the housing outlet.

Another feature of the invention is that the shear pump discs have planar surfaces free of support struts.

A further feature is that the outlet slot in the hollow rotatable shaft is offset from the shaft diameter. Preferably, the slot is defined by substantially parallel, longitudinally extending leading and trailing surfaces. The center line of the slot, midway between the leading and trailing surfaces, is offset from the diameter of the shaft which is parallel with the slot center line.

Yet feature of the invention is that the flow area through the slot is greater than the cross-sectional area of the hollow shaft.

Another feature of the invention is that the flow area at the centers of the discs is greater than the flow area through the slot.

A further feature of the invention is that the discs juxtaposed with the housing walls have flat outer surfaces and tapered inner surfaces.

Further features and advantages of the invention will readily be apparent from the following specification and from the drawings, in which.

The embodiments of the pump illustrated herein are intended for use as a cardiac assist device. The pump has other uses, particularly in pumping liquids which cannot be subjected to turbulence or high forces. For example, volatile or explosive liquids require gentle treatment; and milk is less subject to spoilage when turbulent flow is avoided.

Figure 1:
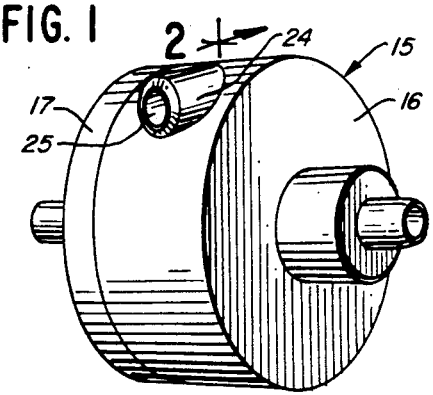
FIG. 1 is a perspective view of the pump.
Figure 3:
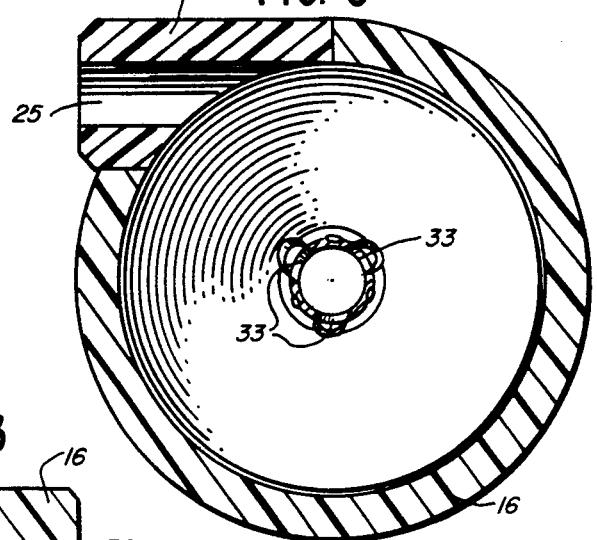
FIG. 3 is an enlarged transverse section taken along line 3—3 of FIG. 2.
Figure 2:
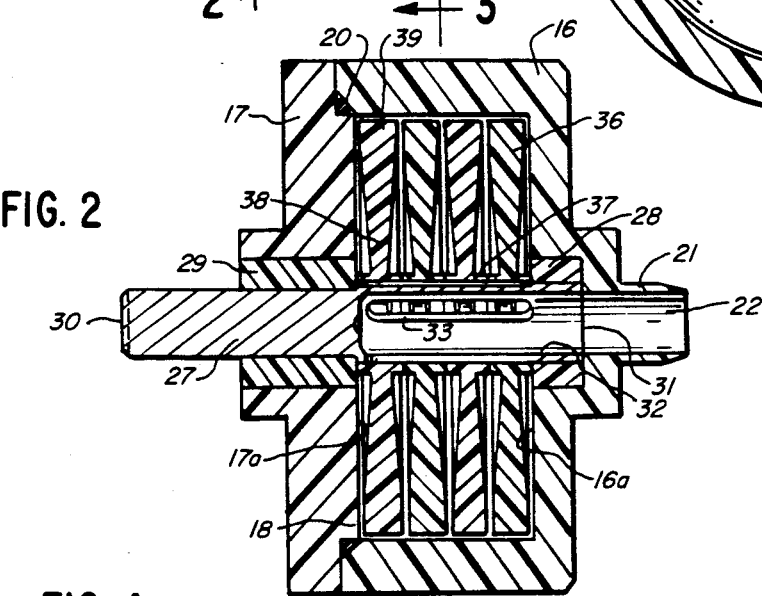
FIG. 2 is an enlarged longitudinal section taken along line 2—2 of FIG. 1.

The pump shown in FIGS. 1, 2 and 3 has a cylindrical housing 15 with a cup-shaped cylindrical body 16 and a circular end plate 17. The interior of body 16 is a cavity with a circular cross-section. End plate 17 has a central boss 18 which extends into the cup-shaped body. The joint between the cover and body is sealed by an O-ring 20; and the cover is secured to the body by an adhesive. An axial nipple 21 extends from the end of body 16 and has an inlet flow passage 22. A tangential nipple 24 extending from the wall of cup-shaped housing 16 has an outlet flow passage 25.

The pump has a rotor which includes rotating shaft 27 journaled in bearings 28, 29 in the pump body 16 and cover 17, respectively. The end 30 of the shaft extending from cover 17, is connected with a suitable motor drive, not shown.

The right portion of shaft 27 as viewed in FIG. 2 is hollow and the right end 31 of the shaft is seated on the interior surface of housing body 16 so that the flow passage 32 through the shaft mates with and is a continuation of the flow path 22 through inlet nipple 21. The rotating shaft acts as a first stage, centrifugal pump. Liquid received through the inlet nipple 21 is discharged through three peripherally spaced, axially extending slots 33 in the wall of the shaft.

Parallel discs 36 mounted on shaft 27 form a second stage shear pump. The shear pump receives liquid at the centers of the discs from the slots 33 in shaft 27 and discharges the liquid between the spaced apart peripheries of the discs to the housing outlet 25.

Each shear pump disc 36 has a hub 37 which fits over the outer surface of the shaft 27 and the slots 33 extend through the disc hubs, as will appear. The disc is tapered radially outwardly from a thin section at the hub to a thick section at the periphery. The axial dimension of the hub is greater than the axial dimension of the disc at the periphery. Thus, with discs on the shaft 27 and the ends of the hubs 37 in engagement, the peripheries of the discs are spaced apart to accommodate liquid flow outwardly to the housing outlet 25. Axially extending, facing grooves 41 in the outer surface of shaft 27 and 42 in the inner surface of disc hub 37 are filled with a key, as a body of epoxy 43, to lock the discs to the shaft.

Several geometric relationships of the pump elements contribute to the gentle action, low turbulence and high efficiency of the pump.

The disc hubs 37 are configured to complement the three slots 33 in shaft 27, as best seen in FIGS. 6–9. The rotor as viewed in FIG. 6 rotates counterclockwise, arrow 45. Slot 33 has a leading surface 47 and a trailing surface 48, the surfaces being parallel to each other. The center line of slot 33, a line 49 parallel with the leading trailing surfaces and equally spaced from them, is offset from the parallel diameter 50 of the shaft. This slot location is sometimes referred to herein as "offset". The width of the slot can be expressed in terms of the angle 51 between radii 52, 53 through the intersections of the leading and trailing slot surfaces with the outer surface of the disc hub. In the pump illustrated, the slot offset is of the order of ¼ the inner diameter of the shaft and the slot width is of the order of 30°. The centerline of each slot intersects the inner surface of hollow shaft 27 at a point displaced 30° from the shaft diameter which is parallel with the slot centerline.

The slots 33 in the disc hub are extended outwardly into the disc body to accommodate liquid flow out of the shaft. The inner surface of the disc body forms a blade 55 having an angle of the order of 90°.

Slots 33 through shaft 27 and the disc hubs 37 provide for unimpeded flow of liquid out of the shaft to the interdisc space. The flow area through the slots is greater than the flow area of shaft 27; and the flow area outwardly between the tapered disc body 36 is greater than the flow area through the slots. This progressive increase in flow area through the pump contributes to the establishment of the desired liquid flow without subjecting the liquid to turbulence or excessive velocity gradients. The area between the discs at the periphery is less than the area at the hubs and at the mean radius of the discs providing greatest shear pumping action where the tangential speed is greatest.

The centrifugal pumping action of the offset slots imparts a whirling motion to the fluid being pumped at the transition from the shaft to the discs. This reduces the forces to which the liquid is subjected and improves the efficiency of the shear pump. The absence of supporting struts between the discs also contributes to reduced turbulence and gentle treatment of the liquid.

The disc hubs 37 adjacent the end walls 16a, 17a of housing body 16 and the housing cover 17 are not slotted. The hubs block outward flow from the shaft 27 along the housing end walls and reduce undesirable recirculation of liquid within the pump.

The pump components are of materials which do not interact undesirably with the liquid pumped. For a blood pump inert materials which do not contaminate blood must be used. If the blood pump is to be implanted, the housing must be a material which is not rejected by the body.

Test models of the pump have had a housing and impeller discs of an acrylic plastic. Shaft 27 is of stainless steel with bearings 28, 29 of a polyamide resin sold under the trademark TORLON by Amoco. Alternatively, the shaft may be a polycarbon material sold under the trademark LEXAN by General Electric with acetyl resin bearings sold under the trademark DELRIN by E. I. DuPont.

A pump used in extracorporeal tests with dogs has a housing with an inner diameter of 3.8 inches and an axial dimension of 1.0 inch. The shear pump discs have a diameter of 3.625 inch and an axial dimension at the periphery of 0.220 inch. The spacing between the discs at the periphery is of the order of 0.025 inch. The shaft 27 has an outer diameter of ½ inch and an inner diameter of 7/16 inch. The pump is designed to operate at a nominal speed of 1200 rpm. In an application where pulsatile blood flow is simulated, the speed may be varied between 400 rpm and 1200 rpm. Each of the three slots 33 has a width of the order of 30°, measured as described above and the slots are offset 7/64 inch.

Figure 4:
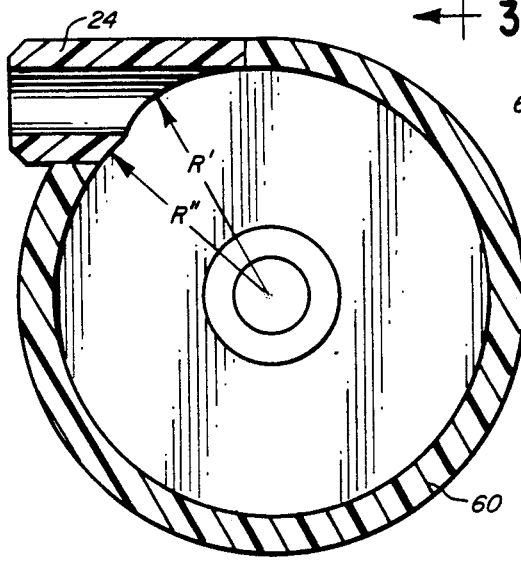
FIG. 4 is a transverse section of the pump housing, similar to FIG. 3, showing a volute configuration of the housing, terminating at the housing outlet.

A modified pump housing 60 is illustrated in FIG. 4. The diameter of the interior of the housing is increased from R" to R', providing a volute configuration which enhances pump efficiency. In the pump described above, R' is of the order of 0.050 inch greater than R".

Figure 5:
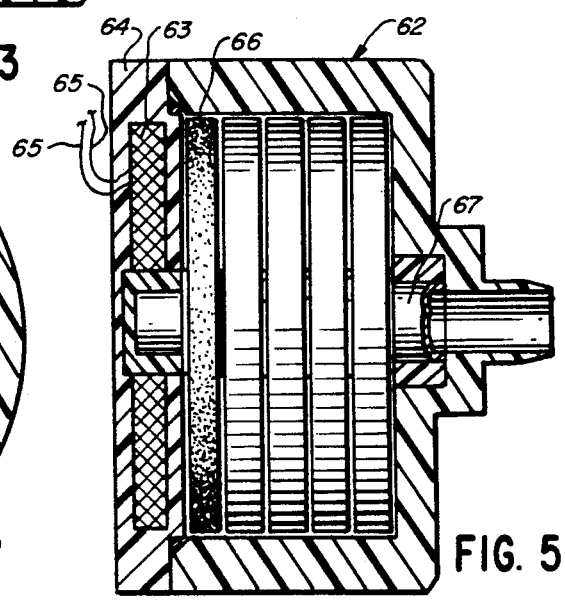
FIG. 5 is a longitudinal section of a pump similar to FIG. 2, with an integral drive motor.
Figure 6:
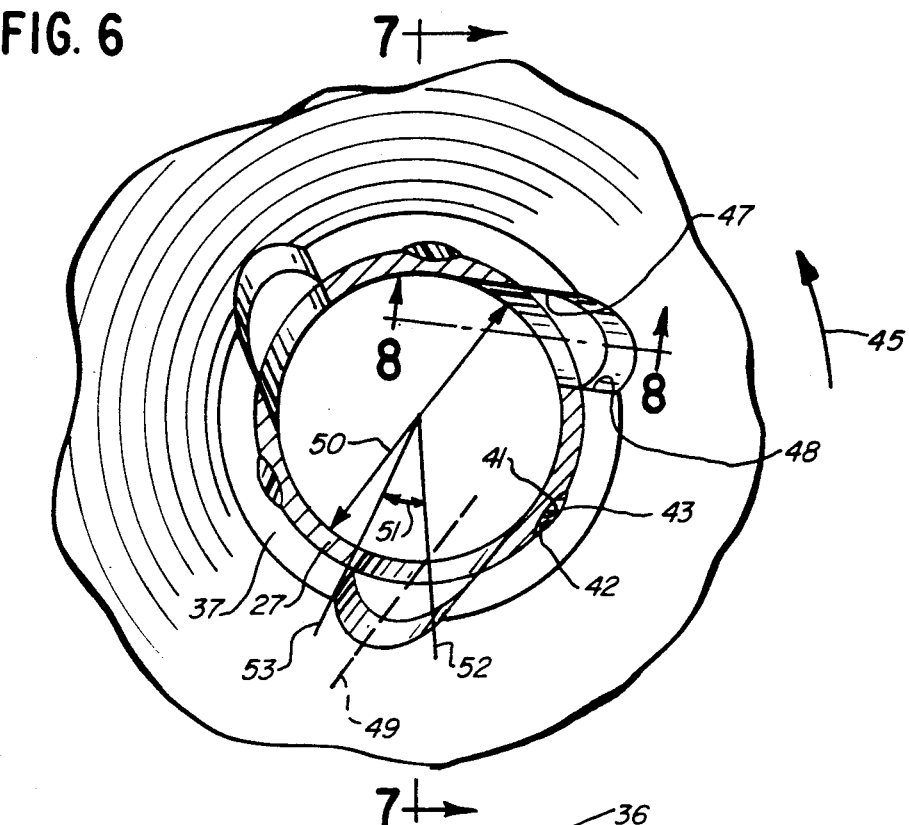
FIG. 6 is an enlarged fragmentary transverse section illustrating the shaft, the center portion of a disc and the centrifugal pump outlet slots.
Figure 7:
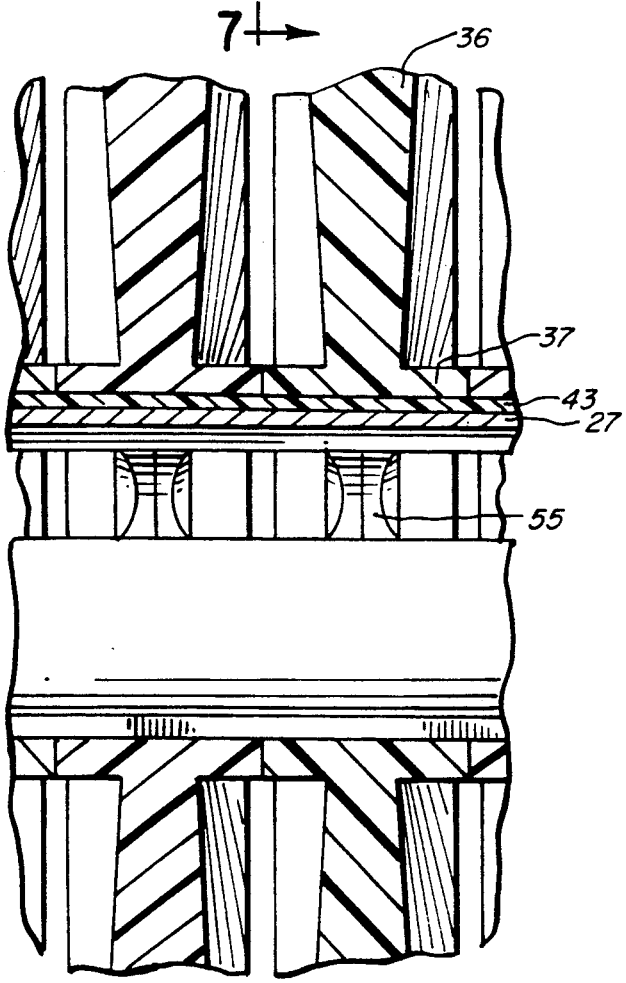
FIG. 7 is an enlarged fragmentary longitudinal section taken along line 7—7 of FIG. 6.
Figure 8:
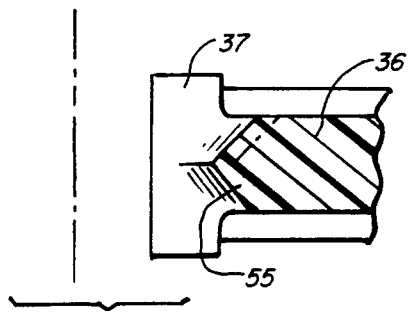
FIG. 8 is an enlarged fragmentary section along line 8—8 of FIG. 6 illustrating the slot through the hub of the disc.
Figure 9:
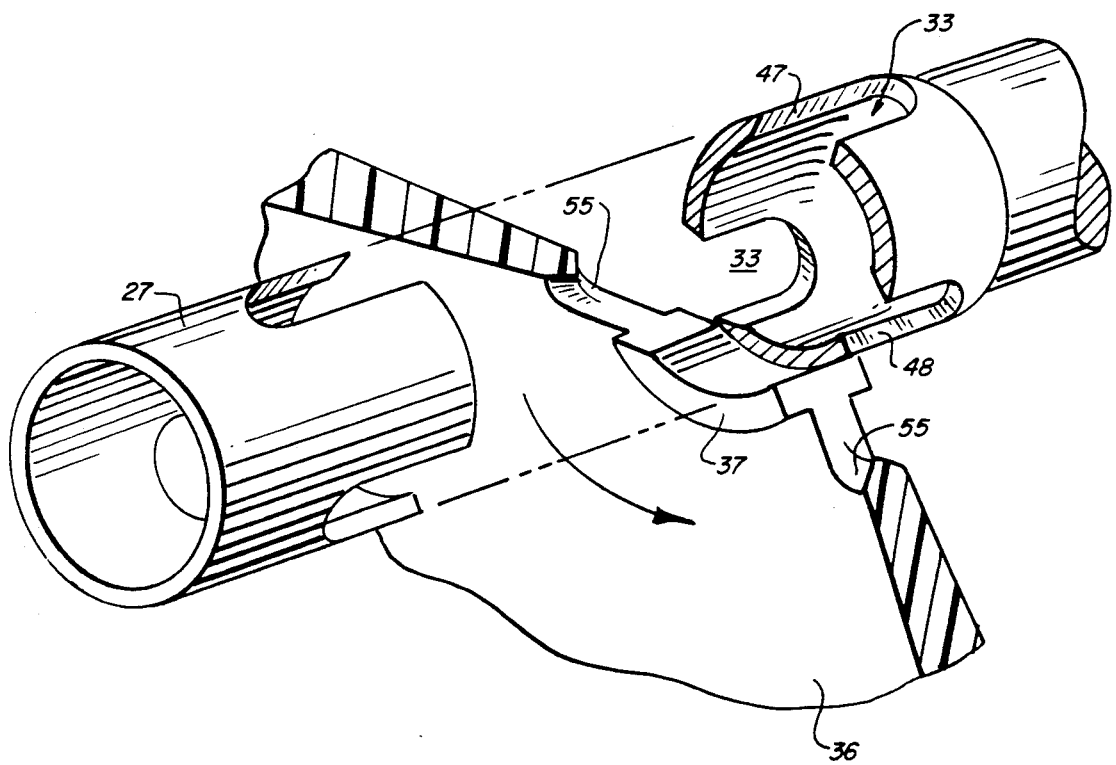
FIG. 9 is an enlarged fragmentary perspective illustrating the shaft, shaft slots and central portion of a disc.

A modified pump 62, FIG. 5, has an integrated electric motor and is designed to be implanted as a cardiac assist device. The motor includes a coil 63 molded in pump cover 64 and having terminals 65 for connection with a driving circuit (not shown) which may be battery powered. The current through coil 63 establishes a rotating magnetic field which interacts with a magnetized disc 66 on shaft 67 to drive the pump. Further details of an implanted flow enhancer are described in Moulder application Ser. No. 442,712 filed Nov. 29, 1989, entitled Cardiovascular Flow Enhancer and Method of Operation.

Figure 10:
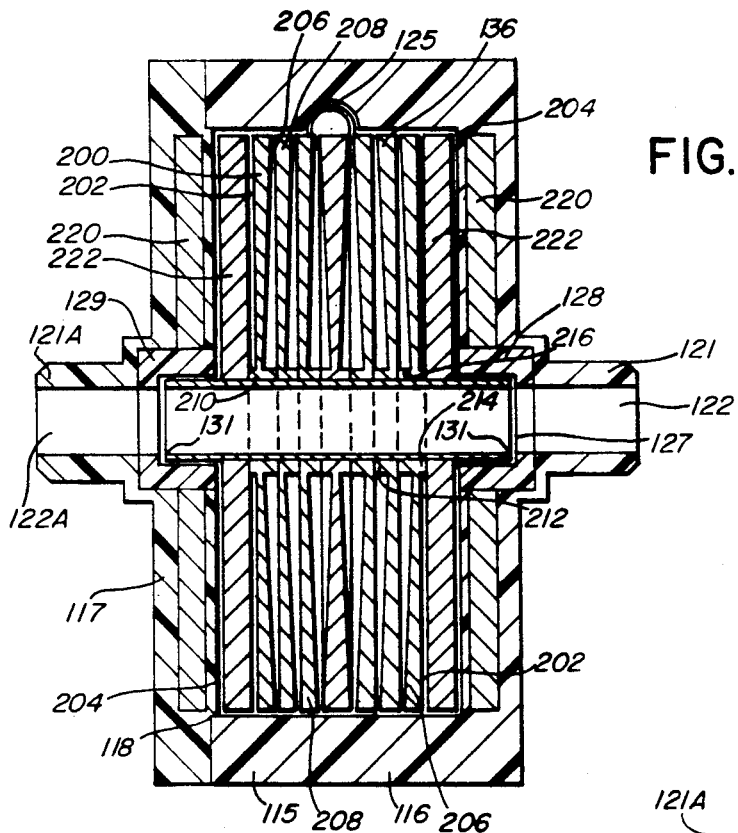
FIG. 10 is an enlarged longitudinal section of an additional embodiment of the pump.
Figure 11:
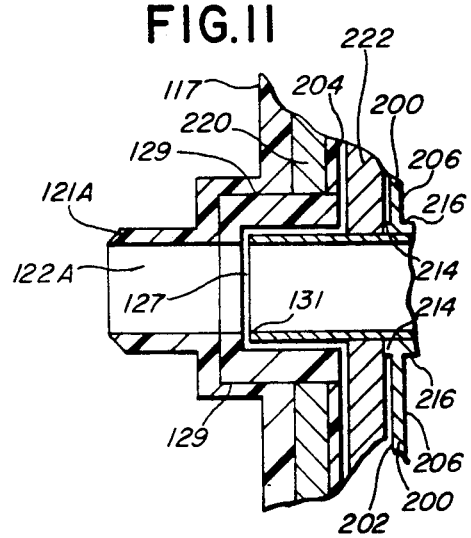
FIG. 11 is an enlarged fragmentary longitudinal section of the FIG. 10 embodiment of the pump.
Figure 12:
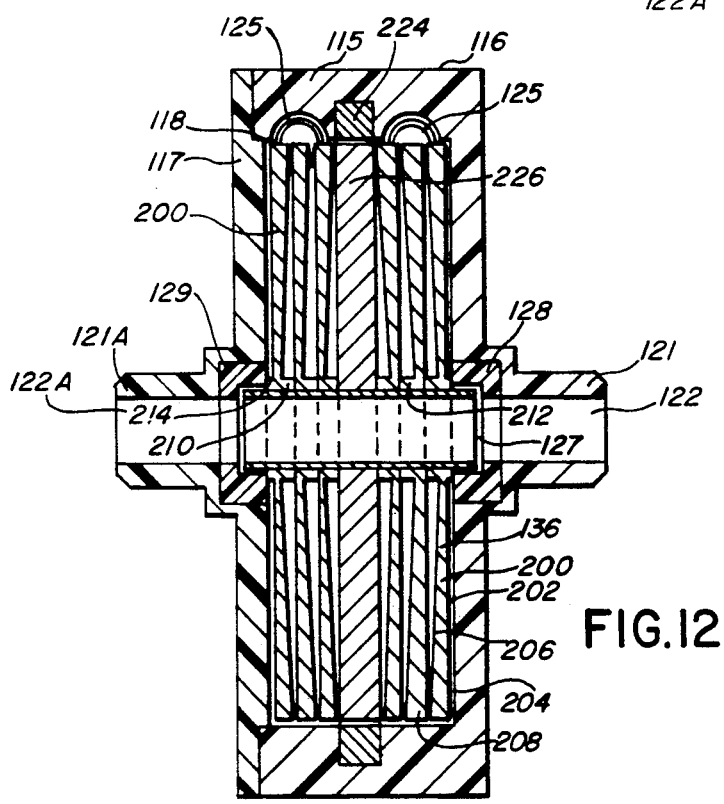
FIG. 12 is an enlarged longitudinal section of an additional embodiment of the pump.

Additional embodiments of the invention are shown in FIGS. 10–12. As in the previously-discussed embodiments, the pumps in the embodiments shown in FIGS. 10–12 include a cylindrical housing 115 with a cup-shaped cylindrical body 116 and a circular end plate 117. The end plate 117 has a central boss 118 which extends into the cup-shaped body. The cover is secured to the body by an adhesive. An axial nipple 121 extends from the end of the body 116 and has an inlet passage 122. In the embodiments shown in FIGS. 10–12, a second axial nipple 121A extends from the end plate 117 and has an second inlet passage 122A. Thus, two inlets, each having a diameter of about 0.375 inches are provided in these embodiments. Outlet flow is provided through outlet passages 125 in the cup-shaped body. In the FIG. 12 embodiment, two parallel outlets, each having a diameter of about 0.3125 inches, are provided.

Also as in the first embodiment, the pumps of FIGS. 12 have a rotor which includes a rotating shaft 127 journaled in axial and thrust bearings 128, 129 in the pump body 116 and cover 117, respectively. The bearings 128, 129 are annular and are stepped to maintain the axial position of the shaft 27. The bearings 128, 129 may be made of a polyamide resin sold under the trademark TORLON by Amoco.

The ends 131 of the shaft 127 are hollow and are seated on the bearings. The bearings 128, 129, axial nipples 121, 21A, and inner diameter of the shaft 127 are dimensioned to provide uniform diameter flow paths through the nipples, bearings and shaft.

In the embodiments shown in FIGS. 10 and 12, the outer diameters of the ends 131 of the rotating shaft 127 are somewhat smaller than the inner diameters of the bearing surfaces upon which the ends 131 are seated. The shaft 127 thereby floats in the bearings 128, 129 with a radial clearance of about 0.002 inches.

A plurality of parallel discs 136 mounted on shaft 127 form a second stage shear pump. The outer discs 200 have flat outer surfaces 202 spaced from and substantially parallel to the inner walls 204 of the housing. In the FIG. 12 embodiment, the flat outer surfaces 202 of the outer discs 200 are spaced about 0.010 inches away from the inner walls 204 of the housing. The outer discs 200 have tapered inner surfaces 206, so that the outer discs taper radially outwardly from a thin section at the rotating shaft 127 to a thick section at the periphery. A plurality of intermediate discs 208 are disposed on the shaft 127 between the outer discs 200. The intermediate discs 208 may be tapered on one side, like the outer discs, or tapered on both sides, as in the first embodiment, or may be a mixture of the two types of discs.

Each outer disc 200 has a hub 210, and each intermediate disc 208 also has a hub 212. The hubs 210, 212 fit over the outer surface of the shaft 127. The axial dimension of the hubs 210, 212 is greater than the axial dimension of the discs 200, 208 at their peripheries so that the peripheries of the discs are spaced apart to accommodate liquid flow outwardly to the housing outlet 125. In the embodiments illustrated in FIGS. 10-12, the gap at the peripheries of the discs is about 0.015 inches. The hubs 210, 212 may be secured to the shaft with a key, as described with respect to the first embodiment.

The hubs 212 of the intermediate discs 208 are configured to complement the slots in the shaft, as in the first embodiment, and may be configured with complementary slots as described with respect to the first embodiment. The hubs 210 of the outer discs 200 have outer portions 214 between the outer surfaces 202 of the outer discs and the inner walls 204 of the housing. These outer portions 214 of the hubs 210 do not have complementary slots, and thereby do not feed blood from the centrifugal pump to the spaces between the outer surfaces 202 of the outer discs 200 and the inner walls 204 of the housing. The lengths of the slots in the rotating shaft may also stop short of the outer portions of the hubs to further minimize liquid flow in this area.

The inner portions 216 of the outer disc hubs 210 adjacent to the hubs 212 of the adjacent intermediate discs 208 may have slots to complement the slots in the shaft. As in the first embodiment, the slots in the intermediate disc hubs 212 and in the inner portions 216 of the outer disc hubs 210 may extend outwardly into the disc body.

The embodiments shown in FIGS. 10-12 include an integrated electric motor. In the FIG. 10 embodiment, the motor includes two coils 220 molded in the end plate 117 and the cup-shaped cylindrical body 116, and having terminals for connection to the driving circuit (not shown) which may be battery powered. The current through coils 220 establishes rotating magnetic fields which interact with a pair of magnetized discs 222 on the shaft 127 to drive the pump. In the FIG. 10 embodiment, the magnetized discs have flat surfaces and are disposed between the flat outer surfaces 202 of the outer discs 200 and the inner walls 204 of the housing 115. The housing outlet 125 in the FIG. 10 embodiment is midway between the magnetized discs 222. In the FIG. 12 embodiment, the coil 224 is molded into the cup-shaped housing 115 around the periphery of a single magnetized disc 226 mounted in the center of the housing on the shaft 127. An equal number of discs are provided on both sides of the central magnetic disc 226, and two outlets 125, one on either side of the magnetized disc 226, are provided. In the FIG. 12 embodiment, the flat outer surfaces 202 of the outer discs 200 are juxtaposed with and spaced from the flat inner walls 204 of the housing 115.

With the flat outer surfaces 202 of the outer discus 200 juxtaposed with the flat inner walls 204 of the housing, as shown in FIG. 12, or with the magnetized discs 222 as in the FIG. 10 embodiment, blood flow in the spaces between the outer discs and the housing should be minimized, thereby reducing the opportunity for thrombosis to occur.

I claim:

1. A liquid pump comprising:
   a housing having an outlet; and
   a rotor in said housing, the rotor having:
   a centrifugal pump first stage with an inlet to receive liquid and an outlet to discharge liquid, and
   a shear pump second stage having an inlet joined with the centrifugal pump outlet to receive liquid therefrom and an outlet to deliver liquid to the housing outlet,
   in which said centrifugal pump is a hollow rotatable shaft connected with said inlet and having an outlet slot therein, said shear pump is a plurality of parallel discs on said shaft, receiving liquid discharged from said shaft slot, the discs being spaced apart at their peripheries to provide an outlet from which liquid is delivered to the housing outlet, the flow area through said slot being greater than the cross-sectional area of the shaft, the flow area at the centers of the discs being greater than the flow area through the slot.

2. The pump of claim 1 in which the housing has volute configuration for delivering liquid from the shear pump outlet to the housing outlet.

3. A liquid pump comprising:
   a housing having an outlet; and
   a rotor in said housing, the rotor having:
   a centrifugal pump first stage with an inlet to receive liquid and an outlet to discharge liquid in which said centrifugal pump is a hollow rotatable shaft connected with said inlet and having an outlet slot therein in which said slots is offset from the shaft diameter, and
   a shear pump second stage having an inlet joined with the centrifugal pump outlet to receive liquid therefrom and an outlet to deliver liquid to the housing outlet.

4. The liquid pump of claim 3 having three slots equally spaced around the shaft.

5. The liquid pump of claim 3 in which said slot is defined by substantially parallel, longitudinally extending leading and trailing surfaces, the center line of the slot, midway between the leading and trailing surfaces, being offset from the diameter of the shaft which is parallel therewith.

6. The liquid pump of claim 5 in which the slot center line is offset from the diameter by a distance of the order of one-fourth the inner diameter of the shaft.

7. A liquid pump comprising:
a housing having an outlet; and
a rotor in said housing, the rotor having:
a centrifugal pump first stage with an inlet to receive liquid and an outlet to discharge liquid in which said centrifugal pump is a hollow rotatable shaft connected with said inlet and having a non-radial outlet slot therein, and
a shear pump second stage having an inlet joined with the centrifugal pump outlet to receive liquid therefrom and an outlet to deliver liquid to the housing outlet.

8. The liquid pump of claim 7 in which there are plural outlet slots spaced peripherally around the rotatable shaft.

9. The liquid pump of claim 7 in which said discs have substantially planar surfaces free of support struts between discs.

10. The liquid pump of claim 7 including an internal drive motor comprising a magnetic disc on said shaft and a motor drive coil in said housing operably associated with said magnetic disc.

11. The liquid pump of claim 7 in which said shear pump is a plurality of parallel discs on said shaft, spaced apart at their centers to provide an inlet at which liquid is received from said shaft slot, the discs being spaced apart at their peripheries to provide an outlet from which liquid is delivered to the housing outlet.

12. The liquid pump of claim 11 in which said housing has bearings for said rotatable shaft.

13. The liquid pump of claim 12 in which the housing has an inlet nipple coaxial with said hollow shaft.

14. The liquid pump of claim 12 in which one end of said shaft extends out of said housing for connection with a drive motor.

15. A liquid pump comprising:
a housing having an outlet; and
a rotor in said housing, the rotor having:
a centrifugal pump first stage with an inlet to receive liquid and an outlet to discharge liquid, and
a shear pump second stage having an inlet joined with the centrifugal pump outlet to receive liquid therefrom and an outlet to deliver liquid to the housing outlet,
wherein said shear pump second stage includes:
a pair of outer discs on said rotor having flat outer surfaces spaced from and substantially parallel to the inner walls of the housing and inner surfaces; and
a plurality of intermediate discs on said rotor between said inner surfaces of said outer discs, said intermediate discs being spaced apart and spaced from the center of the inner surfaces of the outer discs, and providing an inlet at which liquid is received from said centrifugal pump, the outer discs and the intermediate discs being spaced apart at their peripheries to provide an outlet from which liquid is delivered to the housing outlet.

16. The liquid pump of claim 15 wherein said second stage shear pump includes a pair of magnetic discs on said shaft and a pair of motor drive coils in said housing operably associated with said magnetic discs, said magnetic discs being disposed between the housing and the outer discs and having flat inner surfaces spaced from and substantially parallel to the flat outer surfaces of the outer discs.

17. The liquid pump of claim 15 including an internal drive motor comprising a magnetic disc on said shaft and a motor drive coil in said housing operably associated with said magnetic disc.

18. The liquid pump of claim 17 wherein said magnetic disc is disposed midway between said outer discs, with intermediate discs disposed between the magnetic disc and the outer discs.

19. The liquid pump of claim 18 wherein the housing has two outlets, each outlet being disposed near the peripheries of the intermediate discs on either side of the magnetic disc.

20. The pump of claim 15 wherein said centrifugal pump is a hollow rotatable shaft connected with said inlet and having an outlet slot therein, and wherein each disc has a hub extending around said rotatable shaft, the hubs of the intermediate discs each having a slot therein complementary with the outlet slot in the shaft.

21. The pump of claim 20 wherein the hubs of the outer discs have slots complementary with the outlet slot in the shaft, the slots in the outer disc hubs being disposed between the inner surfaces of the outer discs and the adjacent intermediate discs.

22. The liquid pump of claim 20 wherein said intermediate discs are tapered radially to be wider at the periphery than at the center and in which the axial dimension at the periphery is less than the axial hub dimension, to space the peripheries of the discs apart.

23. A liquid pump comprising:
a housing having an outlet; and
a rotor in said housing, the rotor having:
a centrifugal pump first stage with an inlet to receive liquid and an outlet to discharge liquid in which said centrifugal pump is a hollow rotatable shaft connected with said inlet and having an outlet slot therein, and
a shear pump second stage having an inlet joined with the centrifugal pump outlet to receive liquid therefrom and an outlet to deliver liquid to the housing outlet in which said shear pump is a plurality of parallel discs on said shaft, spaced apart at their centers to provide an inlet at which liquid is received from said shaft slot, the discs being spaced apart at their peripheries to provide an outlet from which liquid is delivered to the housing outlet in which each disc has a hub extending around said rotatable shaft, the hubs each having a slot therein complementary with the outlet slot in the shaft.

24. The liquid pump of claim 23 in which the flow area through said slots is greater than the cross-sectional area of the shaft.

25. The liquid pump of claim 23 in which the flow area at the centers of the discs is greater than the flow area through the slots.

26. The liquid pump of claim 23 in which the axial dimension of each disc at its periphery is less than the axial dimension of the hub and the hubs are in engagement along the shaft, spacing the discs apart at their peripheries.

27. The liquid pump of claim 26 in which said discs are tapered radially to be wider at the periphery than at the center and in which the axial dimension at the periphery is less than the axial hub dimension, to space the peripheries of the discs apart.

28. The liquid pump of claim 23 in which said hub and shaft slots have center lines which are offset from the shaft diameter.

29. The liquid pump of claim 28 in which said hub and shaft slots have an angle of the order of 30° at the outer diameter of the disc hubs.

30. The liquid pump of claim 28 in which the center line of each slot intersects the inner surface of the shaft at a point displaced 30° from the shaft diameter parallel with the slot center line.

31. The liquid pump of claim 23 in which the slots in the disc hub extend beyond the hub into the disc body, the inner surface of the disc body forming a blade at each slot.

32. The liquid pump of claim 31 in which said disc body blade has an angle of the order of 90°.

* * * * *